United States Patent
Adsul et al.

(10) Patent No.: US 12,277,701 B2
(45) Date of Patent: Apr. 15, 2025

(54) ASSAY READING METHOD

(71) Applicant: FORSITE DIAGNOSTICS LIMITED, Avon (GB)

(72) Inventors: Neeraj Adsul, York (GB); Marcin Tokarzewski, York (GB)

(73) Assignee: FORSITE DIAGNOSTICS LIMITED, Avon (GB)

( * ) Notice: Subject to any disclaimer, the term of this patent is extended or adjusted under 35 U.S.C. 154(b) by 507 days.

(21) Appl. No.: 17/628,490

(22) PCT Filed: Apr. 22, 2020

(86) PCT No.: PCT/EP2020/061253
§ 371 (c)(1),
(2) Date: Jan. 19, 2022

(87) PCT Pub. No.: WO2021/013392
PCT Pub. Date: Jan. 28, 2021

(65) Prior Publication Data
US 2022/0254133 A1    Aug. 11, 2022

(30) Foreign Application Priority Data
Jul. 19, 2019 (GB) .................................. 1910409

(51) Int. Cl.
*G06T 7/00* (2017.01)
*G01N 33/543* (2006.01)
(Continued)

(52) U.S. Cl.
CPC ..... *G06T 7/0012* (2013.01); *G01N 33/54388* (2021.08); *G06V 10/225* (2022.01); *G06V 10/454* (2022.01); *G06V 10/82* (2022.01)

(58) Field of Classification Search
CPC ........... G01N 33/54388; G01N 33/558; G01N 21/8483; G01N 33/53; G01N 33/5302;
(Continued)

(56) References Cited

U.S. PATENT DOCUMENTS 8,160,348 B2 *   4/2012   Pinard ................... G06T 7/0012
                                                            382/128
9,959,612 B2 *   5/2018   Cauble ................ G01N 15/1433
(Continued)

FOREIGN PATENT DOCUMENTS

CA    2604317 A1 *  2/2009  ......... G06K 9/00127
CA    3117435 C  *  9/2023  ........... G01N 21/274
(Continued)

OTHER PUBLICATIONS

Combined Search and Examination Report for Application No. GB1910409.0, mailed on Jan. 21, 2020, 6 pages.
(Continued)

*Primary Examiner* — Manav Seth (57) ABSTRACT

A computer implemented method for reading a test region of an assay, the method comprising: (i) providing digital image data of a first assay; (ii) inputting the digital image data into a trained convolutional neural network configured to output a first probability, based on the input digital image data, that a first region of pixels of the digital image data corresponds to a first test region of the assay; (iii) if the first probability is at or above a first predetermined threshold, accepting the first region of pixels as a first region of interest associated with the first test region; and (iv) estimating an intensity value of a portion of the first test region in the first region of interest.

17 Claims, 6 Drawing Sheets

(51) Int. Cl.
*G06V 10/22* (2022.01)
*G06V 10/44* (2022.01)
*G06V 10/82* (2022.01)

(58) Field of Classification Search
CPC .... G01N 21/78; G01N 33/52; G01N 21/6428; G01N 2021/8488; G06V 2201/034; G06V 2201/03; G06V 10/225; G06V 10/22; G06V 10/25; G06V 10/70; G06V 10/774–7796; G06V 10/454; G06V 10/82; G06V 30/194; G06T 2207/30004; G06T 7/0012; G06T 2207/20081; G06T 7/90; G06T 7/70; G06T 2207/30072; G06T 7/10; G06T 7/33; G06T 7/97; G06T 2207/20076; G06T 2207/20084; G16H 50/00; G16H 30/00; G16H 50/20; G16H 10/40; G16H 30/40; G06N 3/02–126; G06N 20/00–20; G06N 5/022; G06F 18/214–2155; G06F 7/023; G06F 40/16

See application file for complete search history.

(56) References Cited

U.S. PATENT DOCUMENTS

| | | | |
|---|---|---|---|
| 2010/0045789 A1* | 2/2010 | Fleming | G01N 21/77 348/79 |
| 2019/0302009 A1* | 10/2019 | Borich | G01N 21/8483 |
| 2020/0256856 A1* | 8/2020 | Chou | B01L 3/508 |
| 2021/0172945 A1* | 6/2021 | Armbruster | G01N 33/558 |

FOREIGN PATENT DOCUMENTS

| | | | | |
|---|---|---|---|---|
| WO | WO-2009020972 A2 * | 2/2009 | ......... | G06K 9/00127 |
| WO | WO-2017100652 A1 * | 6/2017 | | |
| WO | WO-2018194525 A1 * | 10/2018 | ............ | G16H 30/40 |
| WO | WO-2019018693 A2 * | 1/2019 | ............ | G06N 20/00 |
| WO | WO-2019215199 A1 * | 11/2019 | ......... | G01N 15/0625 |
| WO | WO-2020120349 A1 * | 6/2020 | ............ | G01N 21/78 |
| WO | WO-2020128146 A1 * | 6/2020 | ........... | A61B 5/1032 |

OTHER PUBLICATIONS

International Search Report and Written Opinion for Application No. PCT/EP2020/061253, mailed on Aug. 4, 2020, 15 pages.

Carrio et al., "Automated Low-Cost Smartphone-Based later Flow Saliva Test Reader for Drugs-of-Abuse Detection", Sensors, Nov. 24, 2015, vol. 15, p. 29569-29593.

Tania et al., "Intelligent image-based colourimetric tests using machine learning framework for lateral flow assays", Computer Science, Jul. 26, 2019, vol. 139, 112843, 22 pages.

Tania et al., "Assay Type Detection Using Advanced Machine Learning Algorithms", 13th International Conference on Software, IEEE, Aug. 26, 2019, pp. 1-8.

Zhao et al., "Object Detection with Deep Learning: A Review", IEEE Transactions on Neural Networks and Learning Systems for Publication, Apr. 16, 2019, 21 pages.

International Preliminary Report on Patentability for Application No. PCT/EP2020/061253, mailed on Feb. 3, 2022, 13 pages.

* cited by examiner

ASSAY READING METHOD

CROSS-REFERENCE TO RELATED APPLICATIONS

This application is a National Phase Application of International Patent Application No. PCT/EP2020/061253, filed on Apr. 22, 2020, which is based on and claims priority to and benefits of British Patent Application No. 1910409.0, filed Jul. 19, 2019. The entire content of all of the above identified applications is incorporated herein by reference.

TECHNICAL FIELD

The present invention relates to a system and computer implemented method for reading assays.

BACKGROUND

Figure 1:
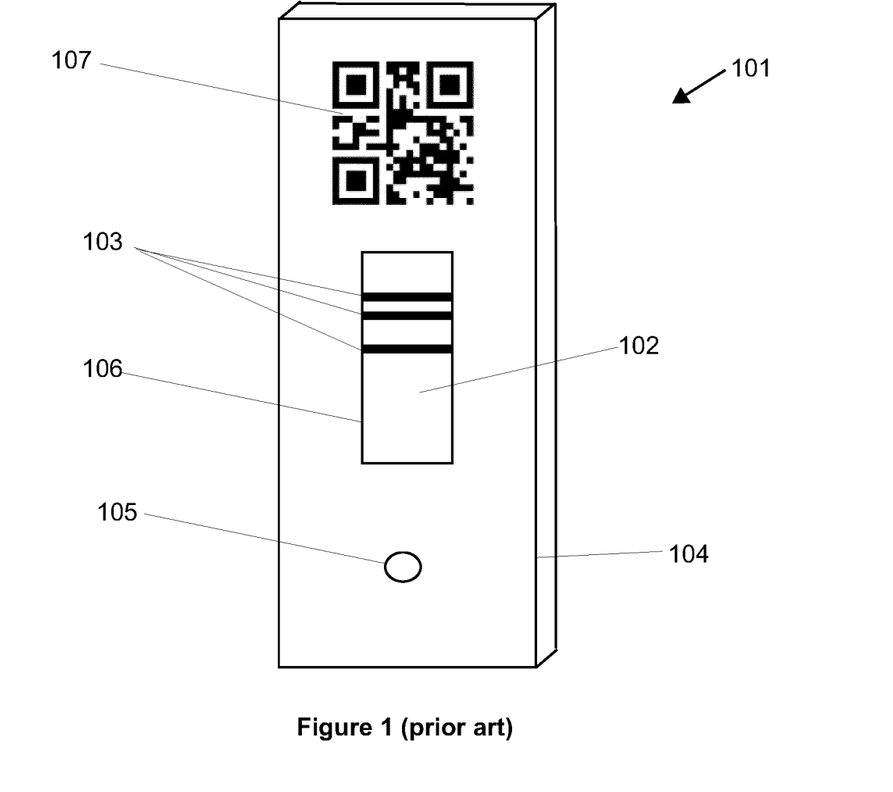
FIG. 1 shows a front view of a known lateral flow test device.

Assays such as lateral flow tests are used to detect the presence or absence of a target analyte (or to quantify the concentration of the analyte(s) in a sample without the need for specialised equipment and are typically used in the field of medical and veterinary diagnostics, biochemistry, agricultural and environmental sciences, molecular biology, and other related fields. With reference to FIG. 1 which shows a known lateral flow test device 101, lateral flow tests normally comprise a test strip 102 with one or more lines of tags, antigens, antibodies or other binding moeities, typically referred to as test lines 103. After a fluid sample is introduced onto the test strip 102, typically through a slot 105, it is spontaneously transported along the length of the strip 102 and prior to that may be transported through a series of pads, which may contain reagents, through the lines of tags, antigens, antibodies or other binding moeities whose interaction with the analyte is designed to provide an optical indication of whether or not the analyte is present. Example labelling particles include gold nano-particles, coloured latex particles, carbon particles and/or fluorescent labels. Typically, the optical indication is provided by a change in colour, hue, and/or intensity of one or more of the test lines 103.

The test strip 102 may optionally be housed in a housing 104 having a slot 105 or opening through which the fluid sample may be introduced. The housing 104 typically has a window 106 through which the test strip 102 and thus the optical indication may be viewed by a user. Additional information about the test manufacturer, test type and expiration date, calibration information such as calibration curve data, and regulatory information may be indicated by a bar code, such as a 2D bar code in an Aztec format, QR code 107, and/or wording. The test strip 102, housing 104, slot 105, window 106 and the other elements described above are known together as a lateral flow test device 101. Other variants of lateral flow test devices include those in un-housed format ("dip-sticks") and a variety of other device architectures are used routinely and will be known to those familiar with the field of lateral flow assays.

Traditionally, the optical indication (i.e. the change in colour and/or hue) of one or more of the test lines was observed, recorded and logged manually by a user. However, manual reading of test results is prone to user error because the optical indication is not always clear and is open to different interpretations. User age, vision, bias, and environmental lighting can all impact how a user interprets a result. Whilst user training can go some way to mitigating user error, this is cumbersome. More recently, digital test device readers have been used to automatically observe and record the optical indication to reduce user error of qualitative, semi-quantitative and quantitative measurements.

Example automatic readers are described in WO2015/121672, WO/2017/203239, WO/2017/203240 and typically comprise one or more light sources and CCD sensors in a closed housing. The assay is inserted into a slot in the closed housing and the test strip illuminated with one or more light sources. The transmitted and/or reflected light is measured by the CCD sensors and the measurements analysed. The margin for user error in these types of devices is small because there is no variance in lighting conditions and data capture inside the closed housing.

Other types of automatic readers are known which rely on cameras of portable user electronic devices such as smartphones. These typically require a user to specify in a UI of a smartphone app which type of lateral flow test device is to be read. The user is then guided to place the test device in a specified position in the field of view of a camera. The correct position and orientation of the test device in the field of view of the camera is based on a priori knowledge of the dimension of the specified test and is indicated to the user by a digital overlay on a user interface of the reader, for example by a red outline turning green when the positioning and orientation is correct. When the test device is positioned and oriented correctly, the reader captures a digital image of the test device on which the test strip is visible. Image processing software may be used to pre-process the image to remove noise from the image. Image recognition software then localises the optical indication on the test strip relative to housing of the device using a priori knowledge of the specified test device, and uses image recognition software to compare the optical indication pixel data with reference data to determine the result of the test/assay. US 2018/0196037A1 proposes such a reader.

A first problem with such readers is that they rely on a single, stationary image that is not live. If the test device in the captured image is oriented incorrectly, or the image is not sharp enough to obtain the desired information from the test strip, cumbersome additional pre-processing steps need to be performed, and in the worst cases the captured image is rejected. Whilst the problem of low quality images can in some cases be mitigated by taking a plurality of images at different contrasts, colour settings, brightness and other image parameters, and then combining these into a single image, this is cumbersome for a user who has to carefully keep the test device in the same position.

A second problem is that the performance of such readers is highly dependent on a priori knowledge of the size and dimensions of the specified test device as this determines where the user is guided to position the test device in the field of view of the camera. The automatic reader may determine that a test device is skew by determining a degree of error associated with any rotational misalignment or skew relative to a previously obtained image of a device in which the positioning and orientation was correct. When the error (i.e. the position and orientation deviation between the present image relative to the previously obtained image) is too high, the automatic reader may reject the image and a new image will need to be obtained.

Further, if a previously unseen test strip/assay or test device is shown to the reader, it is not able to indicate to the user where to position the test device correctly because it has nothing to compare it to. It is thus also not able to localise the test strip and/or accurately read the optical indication until the test device is added to the reader's database of known test devices. Keeping a database of known test devices maintained and up to date with information relating to the latest lateral flow tests or assays is cumbersome and means such readers cannot generalise well to new test devices.

A third problem is that such readers are not able to read multiple lateral flow tests at the same time. If multiple lateral flow tests are present in a captured image, the reader is unable to determine which part of the image belongs to which lateral flow test reader and/or what the error in position or orientation is, and is thus unable to read all of the tests simultaneously. Reading a large number of tests thus takes a long time as each must be read separately.

STATEMENT OF INVENTION

In general terms, the invention provides a computer implemented method for reading a test region of an assay using a trained convolutional neural network.

In one embodiment, a computer implemented method is provided for reading a test region of an assay, the method comprises: (i) providing digital image data of a first assay; (ii) inputting the digital image data into a trained convolutional neural network configured to output a first probability, based on the input digital image data, that a first region of pixels of the digital image data corresponds to a first test region of the assay; (iii) if the first probability is at or above a first predetermined threshold, accepting the first region of pixels as a first region of interest associated with the first test region; and (iv) estimating an intensity value of at least a portion of the first test region in the first region of interest.

Optionally, the digital image data may be of a second assay; the trained convolutional neural network may be further configured to output a second probability, based on the input digital image data, that a second region of pixels of the digital image data corresponds to a second test region of the assay; and the method may further comprise: (i) if the second probability is at or above the first predetermined threshold, accepting the second region of pixels as a second region of interest associated with the second test region; and (ii) estimating an intensity value of a portion of the second test region in the second region of interest.

Optionally, the first test region may be oriented at a skew angle relative to the second test region in the digital image data.

Optionally, the first assay may comprise a housing; the trained convolutional neural network may be further configured to output a third probability based on the input digital image data that a third region of pixels of the digital image data corresponds to the housing; and the method may further comprise: if the third probability is at or above a second predetermined threshold, accepting the third region of pixels as a region of interest associated with the housing; and determining that the first test region is associated with the first assay by determining that the first region of interest is within the third region of interest.

Optionally, the trained convolutional neural network may be further configured to classify the first assay into one or more predetermined classes using features of the first assay.

Optionally, the one or more predetermined classes may comprise assay manufacturer, assay model and/or assay test type; and the features of the first assay may comprise features of the test region and/or features of the housing where present.

Optionally, said estimating may comprise performing thresholding and/or curve fitting on the pixels of the first and/or second regions of interest.

Optionally, the digital image data may comprise video data from an image capture device of a portable user device, and the first, and/or second, and/or third regions of interest may be obtained from different frames of the video data.

Optionally, the convolutional neural network may use one or more of: a MobileNet architecture, and/or a SSD Single Shot MultiBox Detector architecture.

Optionally, said method may be performed on a CPU, GPU and/or on a processor having an architecture optimised for running neural networks.

Optionally, the first assay may be a first lateral flow test device; the first test region may be a first lateral flow test strip of the first lateral flow test device; and the portion of the first test region may be a test line of the first lateral flow test strip.

Optionally, the second assay may be a second lateral flow test device; the second test region may be a second lateral flow test strip of the second lateral flow test device; and the portion of the second test region may be a test line of the second lateral flow test strip.

In one embodiment, a data-processing apparatus is provided comprising means for carrying out the steps of any of the above described methods.

In one embodiment, a computer program is provided comprising instructions which, when the program is executed by a computer, cause the computer to carry out the steps of any of the above described methods.

In one embodiment, a computer-readable storage medium is provided having stored thereon the computer program described above.

In one embodiment, a system for reading an assay is provided, the system comprising: an assay; and a portable user device comprising an image capture device and the computer readable storage medium described above.

Optionally, the assay may comprise a lateral flow test device.

BRIEF DESCRIPTION OF THE DRAWINGS

FIG. 4(*a*) illustratively shows a processing step according to an embodiment of the invention.

FIG. 4(*b*) illustratively shows a processing step according to an embodiment of the invention.

FIG. 4(*c*) illustratively shows a processing step according to an embodiment of the invention.

DETAILED DESCRIPTION

Figure 2A:
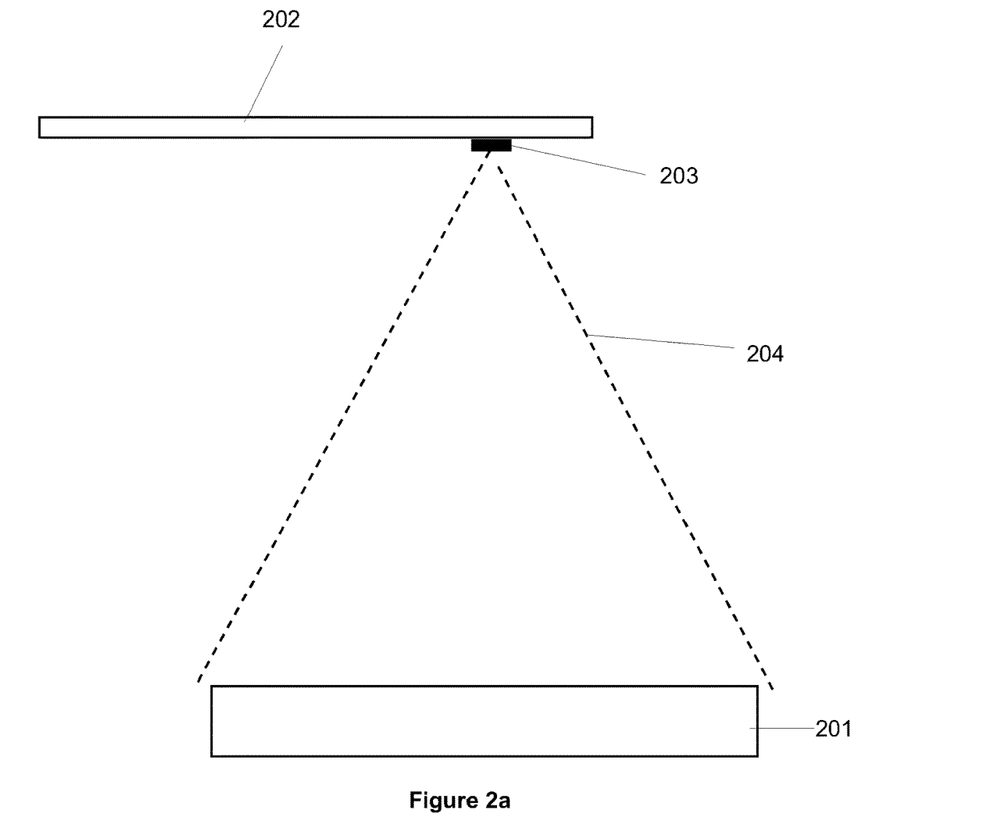
FIG. 2*a* shows a side view of a lateral flow test device and portable user equipment according to an embodiment of the invention.

FIG. 2a shows a side view of a lateral flow test device 201 such as that shown in FIG. 1 imaged by a portable user device 201. The portable user device 201 may be a smartphone, smartwatch, tablet, laptop, or any electronic device and comprises an image capture device 203. The image capture device 203 may be built into the portable user device 201, or may be an accessory component to it. It is envisaged that the image capture device is capable of capturing digital image data of one or more lateral flow test devices 201 and that the digital image data may comprise static images and/or live video. The image capture device 203 has a field of view 204 within which one or more lateral flow test devices 201 are placed when the digital image data is captured.

Figure 2B:
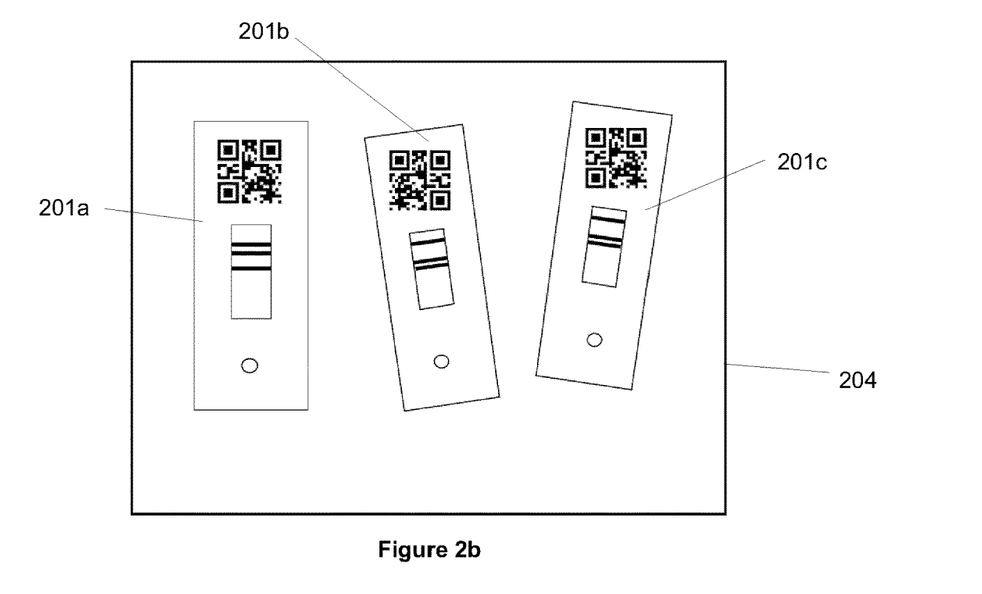
FIG. 2*b* shows a view from an image capture device of the portable user device of FIG. 2*a* according to an embodiment of the invention.

FIG. 2b shows a view as seen from the image capture device 203 of portable user equipment 202 in which a plurality of lateral flow test devices 201a, 201b, 201c are in the field of view 204. Whilst three lateral flow test devices 201a, 201b, 201c are shown in FIG. 2b, any other number of lateral flow test devices may be placed within the field of view 204 in order to be imaged by the image capture device 203. For example, it is envisaged that one, two, three, four, five, or more lateral flow test devices may be placed in the field of view as the image capture device and the number is limited only by the size of the field of view 204.

The one or more lateral flow test devices 201a, 201b, 201c are positioned in the field of view 204 with the test strip facing the image capture device 203. In this way, the captured digital image data includes at least one region of pixels associated with each visible test strip.

Figure 2C:
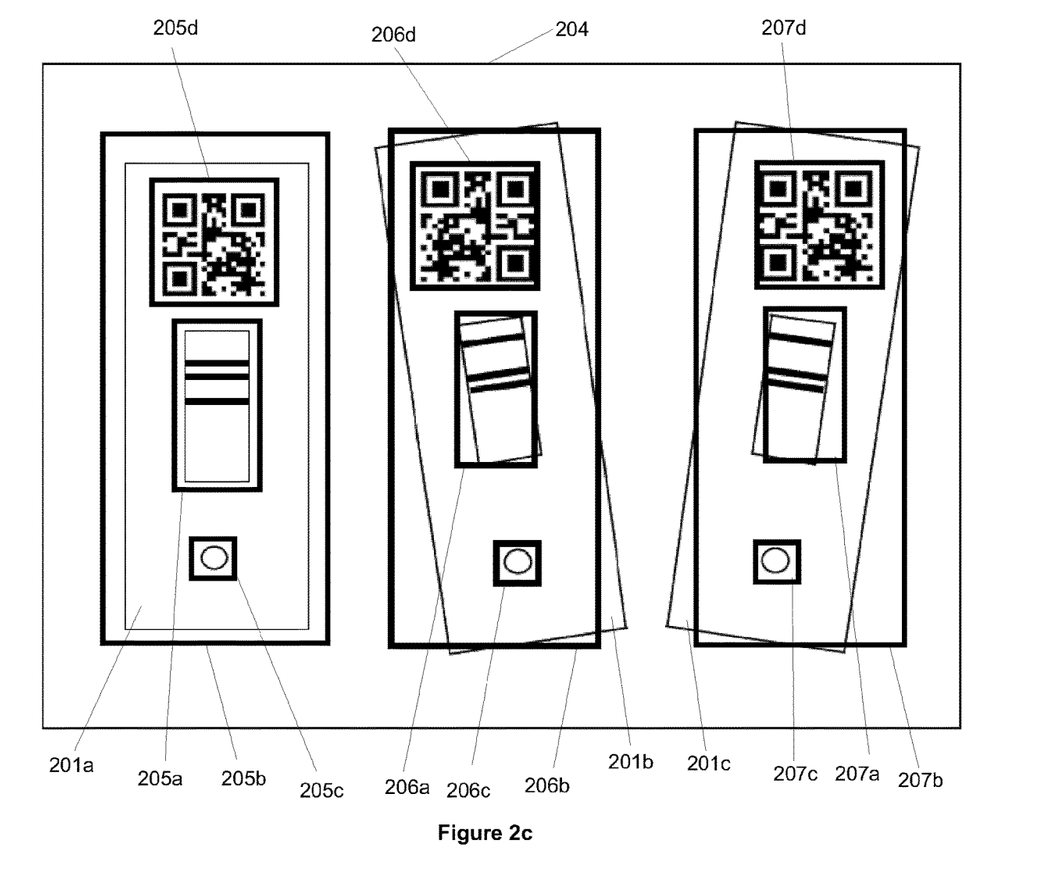
FIG. 2*c* illustratively shows a processing step according to an embodiment of the invention.

FIG. 2c illustratively shows a processing step which may be optional. Following image capture, the digital image data is processed by a processor of the portable user equipment. It is envisaged that the processor of the portable user equipment is a CPU but it may alternatively or additionally be a GPU. The terms "CPU" and "GPU" as referred to herein refer respectively to a central processing unit and a graphical processing unit, the GPU being configured to provide more processing cores running at a lower clock speed than the fewer processing cores of a CPU which run at a higher clock speed.

The digital image data in the example shown in FIG. 2c corresponds to three imaged lateral flow test devices 201a, 201b, 201c but may include any number of such devices as described above. The digital image data is inputted into a trained convolutional neural network which is configured to output a first probability based on the input digital image data that a first region of pixels 205a of the digital image data corresponds to a first lateral flow test strip. If the first probability is at or above a first predetermined threshold, the first region of pixels 205a is accepted as a first region of interest associated with that first lateral flow test strip and thus with the first lateral flow test device 201a.

The inventors have realised that Convolutional neural networks (CNNs) can be used for determining a probability that digital image data correspond to lateral flow test strips. CNNs have been used for image classification tasks. However, running a CNN in real-time is computationally burdensome and traditionally requires powerful graphics processing units (GPUs) which have a high monetary cost compared to cheaper but less powerful central processing units (CPUs).

More recently, a number of CNN architectures or models have been proposed which are more suitable for implementations where computing power is limited, such as is in mobile applications. Three examples of such architectures include:

(1) MobileNets: Efficient Convolutional Neural Networks for Mobile Vision Applications, Andrew G. Howard, Menglong Zhu, Bo Chen, Dmitry Kalenichenko, Weijun Wang, Tobias Weyand, Marco Andreetto, Hartwig Adam, 2017, https://arxiv.org/abs/1704.04861, (2) MobileNetV2: Inverted Residuals and Linear Bottlenecks, Mark Sandler, Andrew Howard, Menglong Zhu, Andrey Zhmoginov, Liang-Chieh Chen, 2018, https://arxiv.org/abs/1801.04381, and (3) SSD: Single Shot MultiBox Detector, Wei Liu, Dragomir Anguelov, Dumitru Erhan, Christian Szegedy, Scott Reed, Cheng-Yang Fu, Alexander C. Berg, 2015, https://arxiv.org/abs/1512.02325.

Optionally, where the digital image data is further of a second lateral flow test device 201b, the trained convolutional neural network is further configured to output a second probability based on the input digital image data that a second region of pixels 206a of the digital image data corresponds to a second lateral flow test strip. If the second probability is at or above the second predetermined threshold, the second region of pixels is accepted as a second region of interest associated with that second lateral flow test strip, and thus with the second lateral flow test device 201b.

The trained convolutional neural network may be further configured to output additional probabilities and accept additional regions of pixels 207a as regions of interest in the same way when further lateral flow test devices 201c are included in the captured digital image data. In this way, multiple lateral flow test devices 201a, 201b, 201c and specifically their test strips may be imaged and recognised as regions of interest simultaneously, something which is not possible with traditional automatic readers. Optionally, the user may specify the total number of lateral flow test devices Where the lateral flow test device or devices also comprise a housing, a slot, and/or additional information such as a QR code, bar code or wording, the trained convolutional neural network may be further configured to output additional probabilities in the same manner as described above for additional regions of pixels of the digital image data, each corresponding to a region of interest 205b, 205c, 205d, 206b, 206c, 206d, 207b, 207c, 207d associated with a respective housing, slot, and/or additional information of a respective device.

Given that each region of interest (205a, 206a, 207a) associated with a lateral flow test strip should be within the region of interest (205b, 206b, 207b) associated with a respective housing. If any region of pixels has an associated probability output by the trained convolutional neural network that is higher than the predetermined threshold but the region of pixels is not in fact within a region of interest associated with a housing, it may be discarded as a false positive, thus leaving only true positives and further improving accuracy of the method.

Further, each region of interest (205b, 206b, 207b) associated with a housing typically has only a predetermined number of lateral flow test strips in it, such as one, two, or more. Each lateral flow test strip may have multiple test lines thereon. In the case where there is only one lateral flow test strip associated with one housing, if multiple regions of pixels in the respective regions of interest (205b, 206b, 207b) associated with the respective housings are found to have a probability above the predetermined threshold that the region corresponds to a lateral flow test strip, only the region with the highest probability within each region of interest (205b, 206b, 207b) is retained such that only a single region of interest associated with a test strip is retained in each region of interest associated with a housing. This technique further improves the accuracy of the method as it ensures that only a single test strip is associated with each housing before further analysis commences. The same concept is applicable where there is more than one lateral flow test strip per housing. In such a case, the predetermined number of test strips is set in advance and only the predetermined number of regions of interest having the highest probabilities are retained.

Optionally, when a region of interest associated with a lateral flow test strip has been determined to be within a region of interest associated with a housing of one of the lateral flow test devices, that lateral flow test strip may be determined to be associated with that specific lateral flow test device. Thus, when multiple lateral flow test devices are imaged and read simultaneously, there is no risk that the wrong lateral flow test strip is associated with the wrong lateral flow test device; a factor which has typically been a problem with known methods and which has prevented existing automatic readers from providing the capability to image and read multiple lateral flow test devices at the same time in a single field of view of an image capture device. Specifically, there is no requirement to keep a separate record of which of the multiple devices is at which position in an image when being read as this information can be inferred from the output probabilities of the trained convolutional neural network by discarding the false positives as described above.

Optionally, the additional information such as QR codes, bar codes, and/or wording, and/or the slots may also be detected using the same techniques as described above and may also be used to discard false positives or false detections. For example, if regions associated with a housing and a lateral flow test strip have been detected but no regions associated with additional information and/or a slot have been detected, the regions may be rejected as false positives. Conversely, if such regions of interest (205c, 205d, 206c, 206c, 207c, 207d) are present, the regions associated with a housing and lateral flow test strip may be retained as true positives or true detections.

Additionally or alternatively, if different types of devices (e.g. different manufacturers, device models, lateral flow test types, etc.) are imaged and read simultaneously, the presence of or lack of these features provides a means to classify and distinguish the different types from each other. For example, a distinguishing feature of one device may be that a slot is in the side rather than the front of the housing so would not be visible from the front. If the front of the devices is imaged and input into the trained convolutional network, the identifying a region of interest associated with the slot may provide an indication that the associated device is the type with the slot on the front, thus providing a means to distinguish between devices. A slot is but one example of a potentially distinguishing feature that may be used to distinguish between devices. Other features which may also be used include without limitation: device branding, logos, mechanical design or even features of manufacturing, engraved or embossed features, vent holes, the geometric shape of the sample port, geometric shaping of the window, and others. These features may be integral with the plastic, or printed on or stuck on as stickers. The trained convolutional neural network may thus comprise a classifier and may be configured to classify the or each lateral flow test device in the captured image data into one or more predetermined classes using any features of the lateral flow test device visible in the image (such as those on the housing where present, or on the test strip or test strip holder when it is not housed, or any other part of the assay which is distinguishable over the background of the captured image). The classifier may be an integral part of the trained convolutional neural network architecture or it may be a separate trained convolutional neural network applied to the extracted regions of interest.

Classification in in this may be achieved by training the convolutional neural network on a training data set comprising a plurality of labelled images of lateral flow test devices such as devices from different manufacturers, different device models, and different lateral flow test types. The labelling may comprise information device size and dimension, and corresponding sizes and dimension of features of the device such as the housing, the slot, the test strip visible through the housing, and/or the additional information such as QR codes, bar codes, and/or wording. Optionally, the training data set may further include images of lateral flow test devices at various orientations and positions in the field of view of the image capture device. These images may be captured manually or may additionally or alternatively comprise synthetic training data obtained by algorithmically adding skewness to non-skew images in the training data. Including such images in the training data ensures the trained convolutional neural network is able to generalise well irrespective of any rotational misalignment or skewness in captured images during test time (i.e. when applied to new, unseen data). Similarly, the convolutional neural network may be trained on training data having variable conditions such as different illumination, shadows, and/or blurriness to ensure the trained convolutional neural network is able to generalise well to these conditions when, during test time, such images are used as input.

Whilst a high degree of variety in the training data and a good ability to generalise is typically advantageous, it can cause the trained convolutional neural to over generalise and generate regions of interest from regions of pixels where the underlying digital image data is of insufficient quality to perform an accurate quantitative measurement. Image quality may be assessed taking into account, for example, illumination conditions, extent of shadows, and blurriness. When all that is required is a binary, qualitative measurement of whether or not a test line is present, this is not problematic. However, in the case of quantitative measurements, the mathematical analysis of pixel values from low quality digital image data is difficult and may result in inconsistent or incorrect results.

In order to address this problem, the variation in the training data may be increased and/or decreased and the convolutional neural network retrained accordingly until the precision and/or recall rate of the trained convolutional neural network is at a predetermined value which balances the ability of the network to generalise whilst ensuring regions of interest are not generated on regions of pixels where the underlying digital image data is below a predetermined quality value (i.e. illumination conditions, extent of shadows, and blurriness). This ensures the regions of interest are not generated when the underlying digital image data quality is too low to perform a quantitative measurement.

Optionally, in order to minimise the effect of low quality image conditions, the present method may include controlling a light source (such as by using a smartphone camera flash as a torch to minimise detrimental shadows caused by the image capture device and other environment light sources such as overhead indoor lighting) to increase or decrease the illumination based on an average of brightness values of the pixels in the region of interest of a previously captured image. Additionally and/or alternatively, the exposure of the image capture device may be controlled (i.e. increased or decreased) to increase quality of the image data in the region of interest, even if this would mean causing overexposure in the parts of the image outside of the region of interest.

In relation to rotational misalignment, the training data may include images where the assays or devices are at any rotational misalignment (such that the trained convolutional neural network can recognise devices or assays at any angle), or only those misaligned by a predetermined angle of, for example, up to 10 degrees, or up to 45 degrees misaligned from a vertical edge of a field of view of the camera. Thus, when a device is imaged which is rotationally misaligned by more than that angle, it is not recognisable over the image background and no region of interest is generated in the first place. In this specific embodiment a device or assay misaligned by more than the predetermined angle is indistinguishable over the background in the image from the point of view of the trained convolutional neural network. In yet a further embodiment, a degree of error associated with a rotational misalignment is determined, and an image is rejected without inputting the image into the trained convolutional neural network.

The training phase may be followed by validation of the trained convolutional neural network with a set of test images which is different from the set of images used for training. It will be appreciated that training and validation is typically carried out by different parties than the end users who will use the trained convolutional neural network in practice to read out test strips.

Following training and validation, the trained convolutional neural network may thus output not only one or more probabilities that a region of pixels is a region of interest associated with a lateral flow test strip, a housing, a slot, and/or additional information such as QR codes, bar codes, and/or wording, but also output a probability that the lateral flow test device with which the region of interest is associated belongs to one or more predetermined classes of devices or assays, by virtue of the presence or lack thereof of distinguishing features of the devices such as those mentioned above including branding, logos, mechanical design or even features of manufacturing, engraved or embossed features, vent holes, the geometric shape of the sample port, geometric shaping of the window, and others.

Optionally, in order to achieve the above functionality, the convolutional neural network may use one or more of: a MobileNet architecture and/or a SSD Single Shot MultiBox Detector architecture. These may be implemented linked together so as to be said to be a single convolutional neural network whereby the output probabilities described above may be intermediate outputs from one or more layers in the network to be passed to a further layer, or the architectures may be implemented in a stand alone manner. Other known architectures may also be used.

Figure 2D:
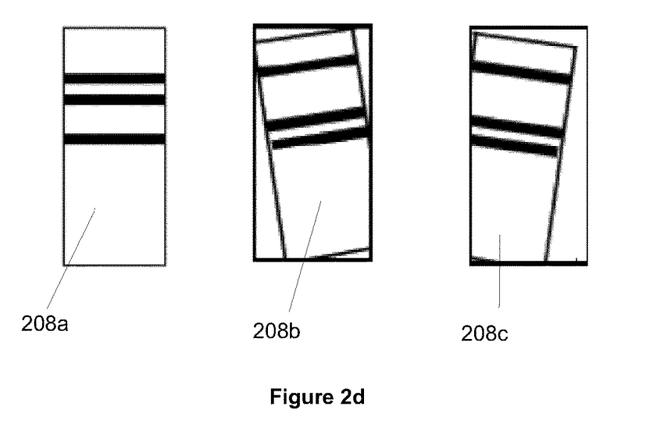
FIG. 2*d* illustratively shows a processing step according to an embodiment of the invention.

FIG. 2d illustratively shows a processing step. Specifically, the regions of pixels corresponding to the test strips 208a, 208b, 208c of the respective lateral flow test devices 201a, 201b, 201c have been accepted as regions of interest despite two of the test strips 208b, 208c in the digital image data being at skew angles relative to the field of view of the image capturing device and the other test strip 208a. As described above, unlike in traditional automatic readers, there is no need to determine a degree of error associated with rotational misalignment or skewness of the lateral flow test device in the captured images or to reject images when the error is above a pre-determined value as the training data with skew, rotationally misaligned images ensures the present method generalises well to skew and rotationally misaligned images.

Once the regions of interest associated with one or more lateral flow test strips have been accepted. The pixel values within these regions are analysed in order to read the results of the test. Specifically, the pixel values of the pixels in each accepted region of interest may indicate one or more of the intensity (i.e. hue, and/or colour) value(s) of the test lines of the associated test strip, and/or other values associated therewith. Pixel values may include, for example, colour component intensities such as red, green, blue, cyan, magenta, yellow, and black component intensities, and/or any other numerical or value associated with that pixel of the image. Thus, by analysing the pixel values within each region of interest, a test line intensity value for each visible test line may be estimated, thus providing an objective, quantitative reading of the or each lateral flow test device in the captured image.

Figure 3A:
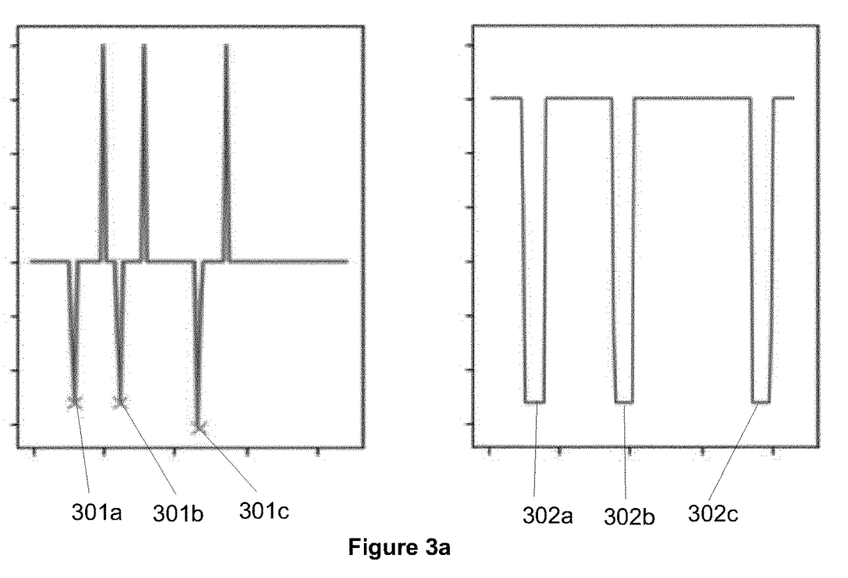
FIG. 3*a* illustratively shows a processing step according to an embodiment of the invention.

FIG. 3a illustratively shows a processing step which may be optional. Estimating an intensity (i.e. hue, and/or colour value(s)) of the test lines from the pixel values may comprise performing thresholding and/or curve fitting on the pixel values of the pixels of the first and/or second region of interest. FIG. 3a shows an illustrative derivative of a curve fitted to the pixel values of an accepted region of interest, and an illustrative graph showing binary values of a line of pixels in an accepted region of interest. The peak positions 301a, 301b, 301c are obtained from the derivative of the fitted curve, and the lower binary values 302a, 302b, 302c correspond to the peak positions.

At its simplest, thresholding is a method of image segmentation in which any pixel value in the image below a predetermined threshold value is changed to a first new value (e.g. white), and any pixel value above the threshold is changed to a second new value (e.g. black). Thresholding thus provides a technique to convert a non-binary multi-colour, multi-pixel value image into a binary image with only two colours or pixel values, or, where a plurality of threshold values are used, a predetermined number of colours or pixel values, which can be processed more easily with simple logic. For example, after thresholding has been performed, a simple Boolean test may be applied to a binary image to determine whether or not one or more lines are present at certain pixel coordinates. Where multi-threshold thresholding is used such that multiple colours or pixel values are present, a simple Boolean test may be applied for each colour or pixel value to determine which lines (if any) are present, and what the intensity value of the respectively detected lines is.

More complex methods of thresholding which may be used include histogram shaped-based, clustering-based, entropy-based, object attribute-based, spatial, local, and hybrid, and multi-banded thresholding methods.

Additionally or alternatively, curve or peak fitting on the pixel values in a chosen coordinate system may be performed to estimate intensity (i.e. hue, and/or colour value(s)) of the test lines. Specifically, a curve is fitted to the pixel values and the positions and widths of the test lines may be found from the derivatives and peak widths of the fitted curve. Simple logic may then again be used to determine whether or not any lines are present at all, and what shape they have. A wider, tall peak may indicate a higher intensity value, whereas a narrow, short peak may indicate a weaker intensity value.

Optionally, before performing either thresholding and/or curve or peak fitting, one or more pre-processing steps may be performed such as baseline correction. This may be performed using iterative methods such as but not limited to asymmetric least-squares smoothing. In one example, once the region of interest is acquired, a 2D low-pass filter may be applied to the whole region of interest (for example a 5×5 smoothing filter) and an average across the post filter values calculated. This results in a one-dimensional (1D) intensity profile obtained from two-dimensional (2D) image capture data. For example, if a region of interest is 20 pixels wide and 70 pixels long, performing baseline correction results in a processed intensity plot which is effectively 1 pixel wide and 70 pixels long. In an alternative, the low-pass filter may be applied directly to the 1D intensity profile after it has been obtained using the above described averaging, this may be described as a 3-point/5-point filter. Other baseline correction techniques such as background subtraction may also be used.

Figure 3B:
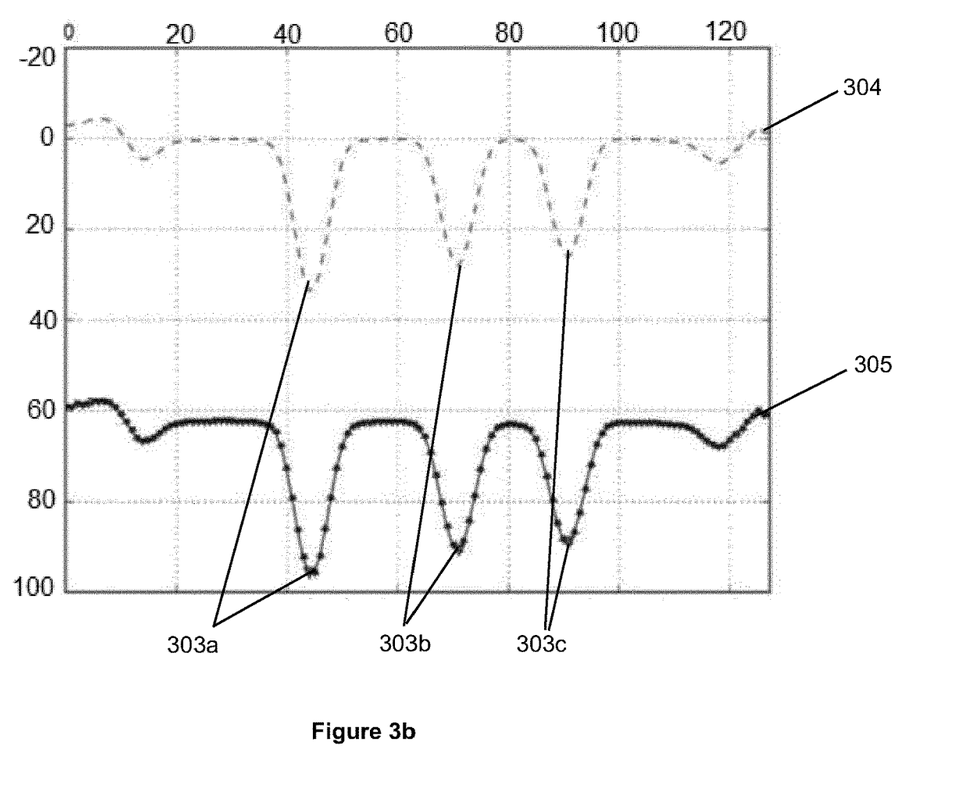
FIG. 3*b* illustratively shows a processing step according to an embodiment of the invention.

An effect of performing baseline correction such as that described above is that the regions of pixels between the test lines (typically corresponding to the blank, nitrocellulose area of the test strip) become set as the background or zero-value against which the peaks and valleys of the intensity profile are measured. FIG. 3b shows a plot indicating the difference between a three peaked 303a, 303b, 303c 1D intensity profile before 305 and after 304 undergoing baseline correction. Specifically, the x-axis may be considered to be the pixel position along the length of an extracted region of interest corresponding to a test strip, and the y-axis may be a corresponding pixel intensity value.

Figure 3C:
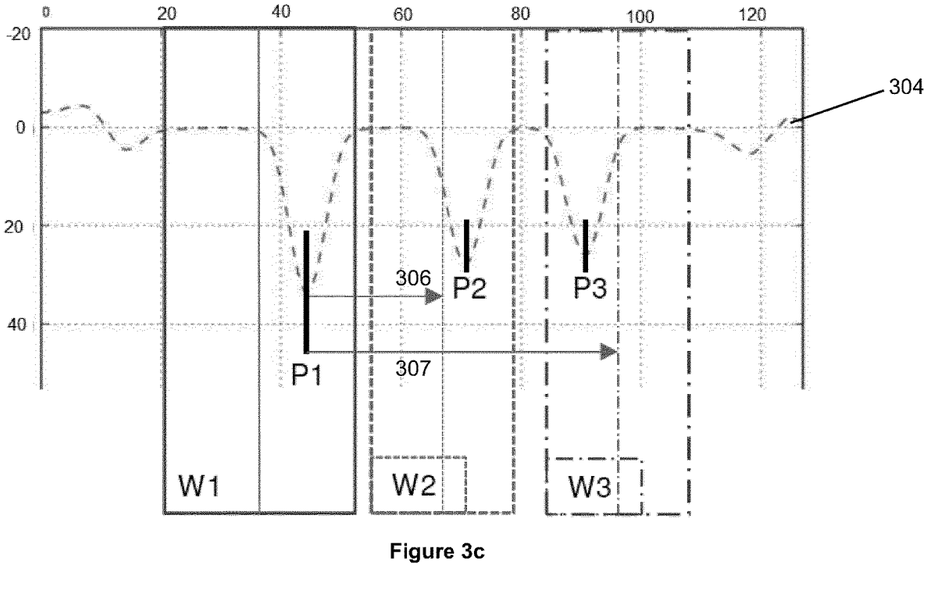
FIG. 3*c* illustratively shows a processing step according to an embodiment of the invention.

Additionally or alternatively, the intensity profile may be analysed using prior knowledge of the expected positions of the test lines within the regions of interest. Specifically, a test strip may have a control line to verify the validity of a test. If the sample has flowed correctly, the control line will appear. If prior knowledge of the positions of the control and test lines and, optionally, positional tolerances is known, the peak positions in the intensity profile will be expected to fall within a certain detection window. This increases the efficiency of the method as it is not necessary to analyse the entire plot to find the peak positions. By way of example FIG. 3c shows an intensity plot 304 after baseline correction has been performed such as shown in FIG. 3b. Prior knowledge of the position and positional tolerance is known in advance so the initial detection windows W1, W2, W3 are set (using e.g. specified ranges of pixels). The peak positions P1, P2, P3 may then be found within these detection windows.

Optionally, the control peak position P1 may be sought first. An advantage of this is that, typically, the distance between the lines on the same strip are consistent but absolute positions may vary. Thus if a control line peak position P1 is found, the test line detection windows W2, W3 may be set or moved to be a specified distance 306, 307 corresponding to the known relative distances between lines. In other words, the search for the other test line peaks P2, P3 is carried out in detection windows W2, W3 whose centre is relative to control line peak position P1. This provides more accurate detection window positioning and thus more efficient and accurate test line peak position detection. The widths of the detection windows W1, W2, W3, may optionally be determined by control and test line positional tolerances, if known.

Optionally, filters or other image pre-processing techniques may be applied to the captured image data prior to performing the above processing and/or intensity value analysis. Specifically, if it is known that a test line is expected to have a certain colour, a custom transform may be applied to obtain a weighted value for a given pixel to convert e.g. a Red-Green-Blue (RGB) channel image into a single intensity channel. Example transforms include: Intensity=a*R+b*G+c*B, or Intensity=a*(R^x)+b*(G^y)+c*(B^z), where a,b,c are [−1.0,1.0] and x,y,z are real numbers.

Other transforms may also be used, for example where the image includes channels other than an RGB channel and/or other linear and/or non-linear transforms. For example, in the most general form, Intensity=f(R,G,B) where f is a linear or non-linear function of the red, green, and blue channels.

Typically, the computational overhead of a CNN increases linearly with the number of pixels and channels per pixel of the input image data. Converting the image by way of a transform as described above (for example by converting the RGB channels into a single channel and/or to a greyscale image) decreases the computational overhead required to run the CNN. Specifically, converting a 24-bit RGB channel image to a 16-bit, or 12-bit greyscale channel image may reduce the computational overhead required by 33% or 50% respectively.

Alternatively or additionally, certain features (such as, for example, colour, shape, edges, contrasts, and/or orientation) in the captured image may be more recognisable than others and may cause neurons or layers in the CNN to activate more strongly than other less-recognisable features. Pre-processing the image to enhance these recognisable features renders the task of training the CNN and running it at test time easier, without materially increasing computational overhead. By way of example, pre-processing input image data to enhance contrast (globally or locally), enhance edges, and/or a combination of these and/or other techniques (which are computationally efficient) prior to inputting it into the CNN, makes the object recognition task of the CNN more accurate because the signal of the recognisable features has been enhanced in the data.

Alternatively or additionally, to reduce computational overhead, the captured digital image data may be cropped prior to being input into the CNN. Specifically, an image capture device of a device such as a smartphone may have a resolution of 1920×1080 pixels. However, only subsample of these pixels actually corresponds to the assay being imaged. A predetermined portion of the outer pixels of the image may be cropped away to reduce the total number of pixels and thus the computational overhead required to run the CNN. For example, cropping a 1920×1080 image to 1500×600 pixels may reduce computational overhead by greater than 40%.

Reducing computational overhead is further advantageous as it either increases speed of computation or it means the CNN may be run in real-time on slower, financially cheaper processors, thereby reducing the monetary cost of an imaging system.

Combining both of the above techniques results in significant improvements in computation speed and/or permits the method to be performed in real-time on slower, cheaper processors.

Once the intensity of the control and/or test lines have been found, they may be output and saved to or recorded in a database together with information identifying which of the lateral flow test devices in the captured image data the test strip was associated with as determined by the retaining of only the test strip region of interest in each housing with the highest probability as described above. Where the trained convolutional neural network was configured to classify the lateral flow test devices into one or more classes as described above, the identified class of that lateral flow test device may also be saved to or recorded in the database and associated with the test strip and the intensity value(s) of the test lines. In this way, multiple lateral flow test devices may be imaged simultaneously, be positioned at skew angles relative to each other and/or relative to the field of view of the image capturing device, and, when enough variety is included in the training data, without any a priori knowledge of the size, dimensions, and other features of the device(s) being imaged.

The digital image data described above may comprise a data from a single, static image, or it may comprise video data from an image capture device such as that integrated in a smartphone, tablet, laptop and/or other portable user device, or a separate accessory connected to such a device. Where the digital image data comprises video data, each of the regions of interest may be obtained from different frames of the video data.

For example, when the first frame of a video is input into the trained convolutional neural network, the output probability for the region of pixels corresponding to the housing may immediately be above the predetermined threshold and so may accepted as a region of interest associated with the housing. However, the output probabilities for the region of pixels corresponding to the test strip, slot and/or additional information may be below the predetermined threshold (e.g. because of a noisy image, dirt, or other imaging issues). In such a case, the information from the first frame localising the housing is present may be retained, and the second, third, and further consecutive frames input into the trained convolutional neural network to attempt to localise any test strips, slots and/or additional information that may be present in the image and specifically in the region of interest associated with the housing. Compared to known methods where images and the information contained therein are rejected or discarded when an error is too large, the present method ensures all information is retained so is more efficient relative to known methods. The present methods thus provide the advantage that a user may continuously capture video until all the necessary information has been obtained, rather than having to manually capture a plurality of single images and discard all of those which could not be read.

When the digital image data is or comprises video data, the present methods also provide the advantage that a user may continuously capture video while the lateral test devices in the field of view of the image capture device changes. For example, the user may manually line up a plurality of 10 or 20 devices and scan over the line of devices with 3-4 devices visible in any given frame of the video. Alternatively, the user may continuously scan an area while he manually moves multiple test devices into and out of the area. Each test strip and the associated results are automatically associated with the correct device as described above although, optionally, known object tracking techniques may also be employed to track each uniquely detected objects across frames to further minimise the risk of duplicate readings. Thus, compared to known techniques, the image capture device need not be manually activated multiple times to image and read multiple devices.

Figure 4:
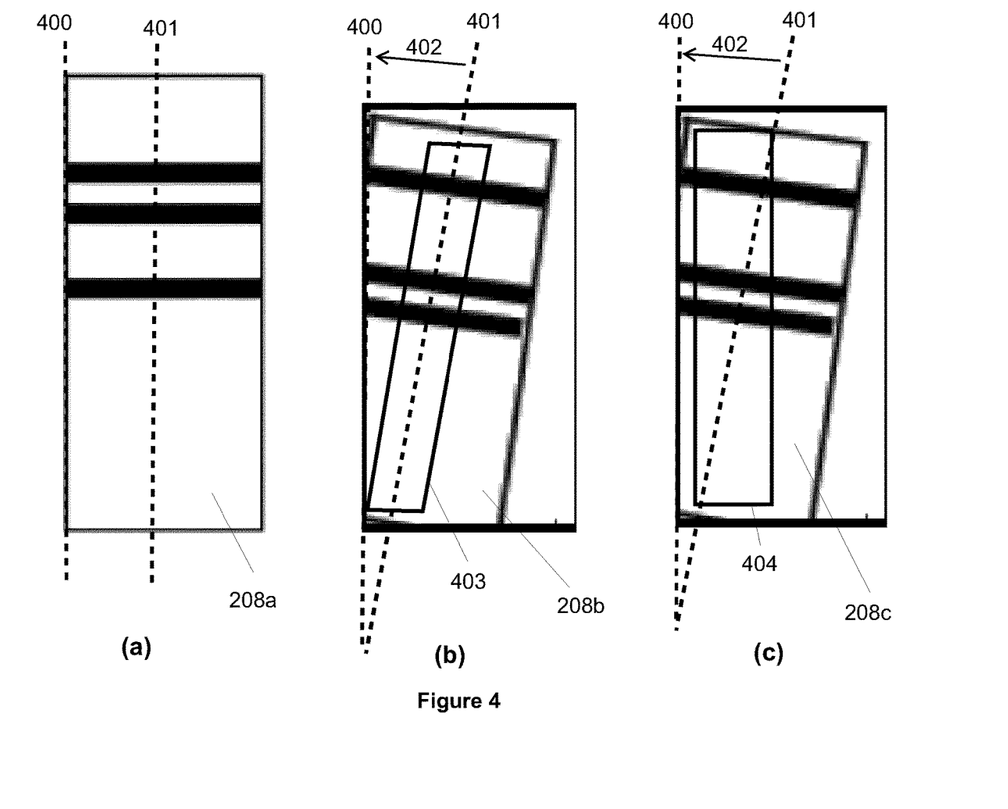

FIGS. 4(a)-(c) illustratively show a number of processing steps, which may be optional. Shown in FIG. 4(a) is an extracted region of interest associated with a test strip 208a. The aspect ratio of the region of interest (that is, the ratio of the pixel width to the pixel height of the region of interest) matches the aspect ratio of the test strip itself (e.g. in SI units). In this case, the line 400 through the pixels along an edge of the region of interest is parallel to a line 401 passing through and being perpendicular to the detected test lines. The rotational misalignment of the test strip is thus zero.

In contrast, in FIGS. 4(b) and 4(c), the aspect ratio of the region of interest does not match the aspect ratio of the test strip 208b, 208c itself. In this case, the line 400 through the pixels along an edge of the region of interest is at an angle 402 relative to the centre line 401 through and being perpendicular to the detected test lines (i.e. the centre line of the test strip). By calculating the aspect ratios of the regions of interest and comparing these to an expected aspect ratio of the test strip 208b, 208c itself (which may be known from, for example the bar code, QR code, other additional information, and/or other a priori knowledge) it can be inferred that the test strip (and thus the lateral flow test device or assay) is rotationally misaligned by an angle 402. In the case of a rectangular test strip of the type shown in FIGS. 4(a)-4(c), the greater the misalignment, the closer the aspect ratio of the region of interest approaches to 1:1. Typically, the misalignment angle for a region of interest with such an aspect ratio will be 45 degrees. Optionally, when an aspect ratio goes beyond 1:1 when rotational misalignment is greater than 45 degrees, a predetermined aspect ratio value or cut-off value may be used to generate a warning that any subsequently estimated test line intensity values may not be accurate, or to stop the processing of that specific image or test strip altogether.

When the aspect ratio indicates that misalignment is present, the region of interest may be cropped to a parallelogram 403 or rectangle shape 404 being a subset of pixels of the original region of interest. The size and dimensions of the parallelogram 403 or rectangle shape 404 may be based on a predetermined percentage of the original region of interest calculated outwards from the above described centre line 402.

An advantage of using cropping instead of attempting to correct the rotational misalignment (e.g. through sheer rotation or area mapping) is that cropping is computationally much more efficient. The cropping of the image ensures that any pixels associated with edges, background or other regions which are not part of the test strip are not used in the subsequent estimation of the test line intensity values. In this way, pixels which would otherwise introduce errors into the quantitative and semi-quantitative measurements are excluded without the need to correct the image for rotational misalignment or determine a degree of error associated with the rotational misalignment suitable for the purpose of such a correction. The present methods thus provides an advantage over such correction techniques because they are computationally more efficient and may be run on devices where processing power is at a premium such as in smartphones.

An advantage of using a rectangle shape 404 over a parallelogram 403 is that an even smaller portion of the region of interest may be used, thus further reducing the risk any pixels outside this portion may cause errors in the quantitative or semi-quantitative measurements.

Of course, whilst a rotational misalignment of up to 45 degrees is described above, it is envisaged that the same techniques may be used to avoid errors in quantitative and semi-quantitative measurements where the rotational misalignment is up to 10 degrees, or is up to 90 degrees or even 180 degrees in either direction. Whether or not this optional technique is necessary will also depend in part on how well the trained convolutional neural network is able to generalise to rotated test strips which in part depends on the rotational variation present in the training data.

As described above, it is envisaged that present methods may be performed on a GPU or CPU, or a combination of both (i.e. where some operations are performed on a GPU and some on a CPU and a means to communicate between them is provided). Additionally, it is envisaged that the present methods may be performed on a dedicated neural network processor having an architecture optimised to run neural networks. Typically, however, trained convolutional neural networks run more efficiently on GPUs particularly when real-time operation is required as may be the case during the reading of lateral flow test devices. GPUs are financially more expensive and portable user devices on which the present methods are envisaged to be run may not have one or, where they do, it may not be computationally powerful and/or the device may not be configured to permit the GPU to run any applications other than those associated with the device's graphics display.

Thus, a method in which the entire processing pipeline is performed with a trained convolutional neural network architecture would not run fast enough for real-time operation on portable user devices. In order to overcome this problem, the present method only uses the above described trained convolutional neural network to determine probabilities that a given region of pixels corresponds to a given feature. Once this is performed, the step of estimating an intensity value of any test lines that are present is performed separately from the convolutional neural network architecture, which is computationally more efficient that performing this step with a convolutional neural network (for example by training it to classify different pixel intensity values into different intensity classes). Thus, by combining convolutional neural network techniques with non-neural network based techniques, the present methods may be implemented to run efficiently in real time using only a CPU, and/or a weaker GPU if one is accessibly provided. It is envisaged that both single and/or multicore CPUs and GPUs may be used with any variety of architectures which will be known to the skilled person.

Figure 5:
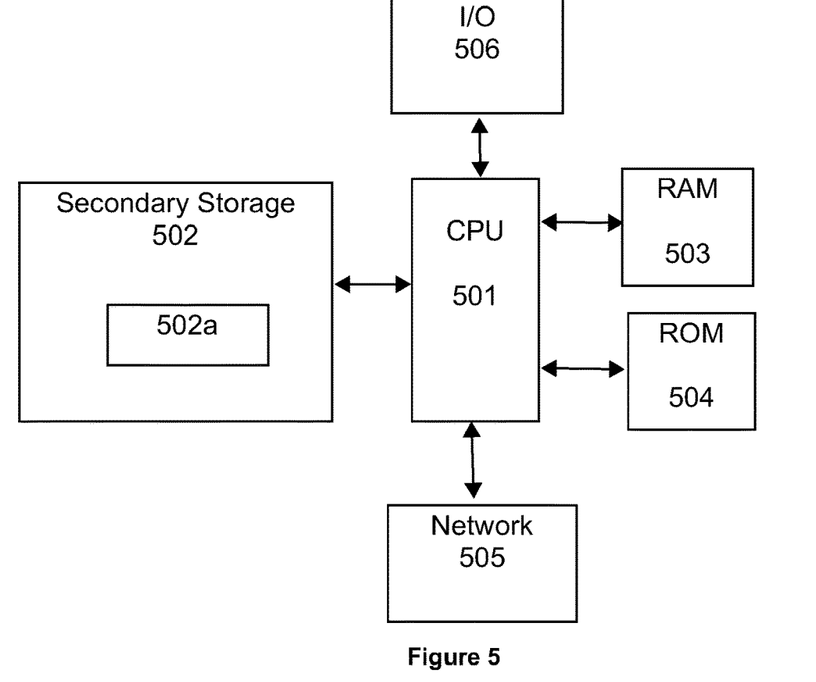
FIG. 5 shows technical architecture according to an embodiment of the invention.

Also provided herein, as shown by the technical architecture in FIG. 5, is an exemplary data-processing apparatus comprising means for carrying out the steps of the methods of any of the above embodiments. As described above, in some embodiments the steps are carried out entirely on a CPU which is cheaper than a GPU.

The data-processing apparatus may comprise a processor 501 that is in communication with memory devices including secondary storage 502 (such as disk drives), random access memory (RAM) 503, read only memory (ROM) 504. The processor 501 may be implemented as one or more GPU chips, CPU chips, which are cheaper than GPUs, and/or dedicated neural network processors having architectures and engines optimised to run neural networks. Illustrative examples of such systems include the iPhone™ Neural Engine™ and Android™ Neural Processing Unit™. The data-processing apparatus may further comprise network connectivity devices 505, and input/output (I/O) devices 506.

The secondary storage 502 is typically comprised of one or more disk drives or tape drives and is used for non-volatile storage of data and as an over-flow data storage device if RAM 503 is not large enough to hold all working data. Secondary storage 502 may be used to store programs which are loaded into RAM 503 when such programs are selected for execution.

In this embodiment, the secondary storage 502 has an order processing component 502a comprising non-transitory instructions operative by the processor 501 to perform various operations of the method of the present disclosure. The ROM 504 is used to store instructions and perhaps data which are read during program execution. The secondary storage 502, the RAM 503, and/or the ROM 504 may be referred to in some contexts as computer readable storage media and/or non-transitory computer readable media.

I/O devices 506 may include printers, video monitors, liquid crystal displays (LCDs), organic LED displays, e-ink displays, plasma displays, touch screen displays, keyboards, keypads, switches, dials, mice, track balls, voice recognizers, card readers, paper tape readers, or other well-known input devices.

The network connectivity devices 505 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), world-wide interoperability for microwave access (WiMAX), near field communications (NFC), radio frequency identity (RFID), and/or other air interface protocol radio transceiver cards, and other well-known network devices. These network connectivity devices 505 may enable the processor 501 to communicate with the Internet or one or more intranets. With such a network connection, it is contemplated that the processor 501 might receive information from the network, or might output information to the network in the course of performing the above-described method operations. Such information, which is often represented as a sequence of instructions to be executed using processor 501, may be received from and outputted to the network, for example, in the form of a computer data signal embodied in a carrier wave.

The processor 501 executes instructions, codes, computer programs, scripts which it accesses from hard disk, floppy disk, optical disk (these various disk based systems may all be considered secondary storage 502), flash drive and other solid-state drives, ROM 504, RAM 503, or the network connectivity devices 505. While only one processor 501 is shown, multiple processors may be present. Thus, while instructions may be discussed as executed by a processor, the instructions may be executed simultaneously, serially, or otherwise executed by one or multiple processors.

Although the technical architecture is described with reference to a computer, it should be appreciated that the technical architecture may be formed by two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the technical architecture to provide the functionality of a number of servers that is not directly bound to the number of computers in the technical architecture. In an embodiment, the functionality disclosed above may be provided by executing the application and/or applications in a cloud computing environment. Cloud computing may comprise providing computing services via a network connection using dynamically scalable computing resources. A cloud computing environment may be established by an enterprise and/or may be hired on an as-needed basis from a third party provider.

It is understood that by programming and/or loading executable instructions onto the technical architecture, at least one of the CPU 501, the RAM 503, and the ROM 504 are changed, transforming the technical architecture in part into a specific purpose machine or apparatus having the novel functionality taught by the present disclosure. It is fundamental to the electrical engineering and software engineering arts that functionality that can be implemented by loading executable software into a computer can be converted to a hardware implementation by well-known design rules.

Also provided herein is a computer program and a computer-readable storage medium for storing the computer program, comprising instructions which, when the program is executed by a computer, cause the computer to carry out the steps of the methods of any of the above embodiments.

Figure 6:
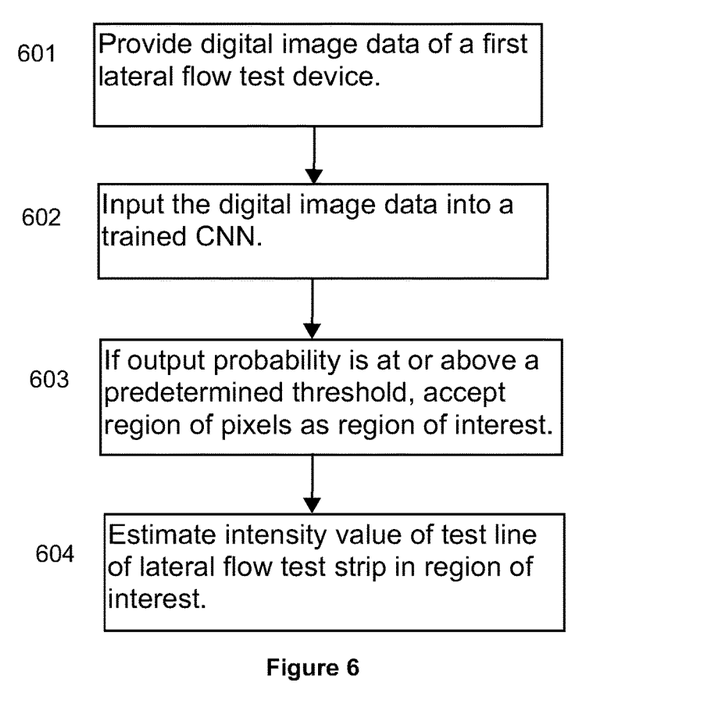
FIG. 6 is a flowchart of a method according to an embodiment of the invention.

FIG. 6 is a flowchart showing method steps according to the above described embodiments that may be performed on the above described data-processing apparatus. Specifically, the method comprises providing 601 digital image data of a first lateral flow test device, inputting 602 the digital image data into a trained convolutional neural network configured to output a first probability based on the input digital image data that a first region of pixels of the digital image data corresponds to a first lateral flow test strip. If the first probability is at or above a first predetermined threshold, accepting 603 the first region of pixels as a first region of interest associated with the first lateral flow test strip, and estimating 604 an intensity value of a test line of the first lateral flow test strip in the first region of interest.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

For example, whilst the above description has been described in the context of a lateral flow test strip of a lateral flow test device, the present computer implemented methods may be applied to any assay with which a quantitative or semi-quantitative measurement is to be performed, and for which a convolutional neural network may be trained to output a probability that regions of pixels are regions of interest based on input digital image data. Specifically, as long as the assay has recognisable or distinguishing features which are visible to an image capture device, a convolutional network may be trained to output probabilities for regions of pixels which may be accepted as regions of interest associated with the recognised features. The regions of interest may then be extracted and further processed separately from the convolutional neural network architecture to estimate intensity values. Thus, the present methods are not limited to use with housed or un-housed lateral flow strips, but are also envisaged to be used with dipstick assays and any other assays (being housed or otherwise) having a test region with optical indicator (such as a colour change) that a chemical reaction has occurred. Specifically, the trained convolutional neural network may be configured to output a probability based on the input digital image data that a region of pixels of the digital input data corresponds to a test region of the assay.

Similarly, the same techniques described above relating imaging multiple lateral flow test devices at the same time may also be applied to imaging a plurality of any assays at the same time. The techniques described above relating to imaging multiple lateral low test strips oriented at skew angles relative to each other may also be applied to imaging a plurality of any assays at skew angles relative to each other. The techniques described above to associate specific regions of interest associated with a housing to a specific lateral flow test device may be applied to any features of assays. For example, in a non-housed assay such as a non-housed lateral test strip or dipstick, there may be a handle or other recognisable feature whose associated region of interest may be used in the same as way as the regions of interest associated with the housing described above. The techniques described above to classify the lateral flow test device into one or more predetermined classes may be applied to any type of assay. The techniques described above relating to performing estimating intensity values by performing thresholding and/or curve fitting may be applied to any type of assay. The techniques described above relating to using video data and obtaining the regions of interest from different frames of the video data may be applied to any type of assay. The techniques described above relating to using MobileNet and/or SSD Single Shot MultiBox detector architectures may be applied to any type of assay. The techniques described above relating to performing the methods on a CPU, GPU and/or on a processor having an architecture optimised for running neural networks may be applied to any type of assay.

It is also envisaged that all of the above techniques may be used with not only colourimetric tests but also with fluorescent tests. Specifically, as long as an intensity value is measurable (as would be the case with fluorescent labels illuminated with a suitable wavelength) the above described techniques may be used. An example fluorescent technique uses green fluorescent protein (GFP).

The invention claimed is:

1. A computer implemented method for reading a test region of an assay, the method comprising:
  (i) receiving digital image data of a first assay, the digital image data comprising at least one region of pixels corresponding to a first test region of a first assay and at least one region of pixels corresponding to a housing of the first assay;
  (ii) inputting the digital image data into a trained convolutional neural network configured to output, for the input digital image data:
    a first region of pixels of the input digital image data corresponding to the first test region of the assay, and a first probability that the first region of pixels corresponds to the first test region; and
    a second region of pixels of the input digital image data corresponding to the housing of the first assay, and a second probability that the second region of pixels corresponds to the housing,
  (iii) if the first probability is at or above a first predetermined threshold, reading the first test region by estimating an intensity value of at least a portion of the first test region in the first region of pixels,
  wherein estimating the intensity value comprises performing thresholding on the pixels of the first region of pixels and the second region of pixels, wherein said thresholding comprising replacing any pixel value in the input digital image data below a predetermined threshold value to a first new value, and any pixel value above the threshold to a second new value;
or otherwise discarding the first region of pixels; and
(iv) when the second probability is at or above a second threshold value, determining that the first test region is associated with the first assay by determining that the first region of pixels is within the second region of pixels.

2. The computer implemented method according to claim 1,
wherein the trained convolutional neural network is further configured to output a third region of pixels of the input digital image data corresponding to a second test region of the assay, and a third probability that the third region of pixels corresponds to the second test region; and
wherein the method further comprises:
if the second probability is at or above the first predetermined threshold, reading the second test region by estimating an intensity value of at least a portion of the second test region in the second region of pixels, or otherwise discarding the third region of pixels.

3. The computer implemented method according to claim 1, wherein the trained convolutional neural network uses a MobileNet architecture, and/or an SSD Single Shot Multi-Box Detector architecture.

4. A data-processing apparatus comprising a processor and a memory configured to store computer instructions, wherein the processor is configured to execute the computer instructions to carry out the steps of the method of claim 1.

5. A non-transitory computer readable storage medium storing a computer program comprising instructions which, when the program is executed by a computer, cause the computer to carry out the steps of the method of claim 2.

6. A system for reading an assay, the system comprising:
a first assay; and
a portable user device comprising an image capture device and the non-transitory computer readable storage medium of claim 5.

7. The system according to claim 6, comprising a second assay.

8. The system according to claim 7, wherein the first assay and the second assay respectively comprise a first lateral flow test device and a second lateral flow test device.

9. The system according to claim 8,
wherein the first test region is a first lateral flow test strip of the first lateral flow test device; and
wherein the portion of the first test region is a test line of the first lateral flow test strip.

10. The system according to claim 9,
wherein the second test region is a second lateral flow test strip of the second lateral flow test device; and
wherein the portion of the second test region is a test line of the second lateral flow test strip.

11. The system according to claim 10, wherein the first test region of the first lateral flow test device is oriented at a skew angle relative to the second test region of the second lateral flow test device.

12. The system according to claim 6, wherein the image capture device is configured to capture the digital image data as video data.

13. The computer implemented method according to claim 1, further comprising training a convolutional neural network on a training data set comprising a plurality of images of lateral flow test devices to obtain the trained convolutional neural network.

14. The computer implemented method of claim 13, wherein the training data set further comprises images of lateral flow test devices at different orientations and positions in a field of view of an image capture device.

15. The computer implemented method of claim 13, wherein the training data comprises images where lateral flow devices are placed at any rotational misalignment from a vertical edge of a field of view of an image capture device.

16. The computer implemented method of claim 13, wherein the training data comprises images where lateral flow devices are placed at a rotational misalignment up to 10 degrees, or up to 45 degrees from a vertical edge of a field of view of an image capture device.

17. The method of claim 1, wherein the first new value is white and wherein the second new value is black.

* * * * *